(12) United States Patent
Yusuf et al.

(10) Patent No.: US 7,595,201 B2
(45) Date of Patent: Sep. 29, 2009

(54) DEVICE FOR MEASURING AN ANALYTE

(75) Inventors: Salim Yusuf, Carlisle (CA); Jack Hirsh, Burlington (CA); John Eikelboom, Canning (AU)

(73) Assignee: McMaster University, Hamilton, Ontario ( * ) Notice: Subject to any disclaimer, the term of this patent is extended or adjusted under 35 U.S.C. 154(b) by 299 days.

(21) Appl. No.: 10/670,118

(22) Filed: Sep. 24, 2003

(65) Prior Publication Data

US 2004/0126826 A1    Jul. 1, 2004

Related U.S. Application Data

(63) Continuation-in-part of application No. PCT/CA03/00422, filed on Mar. 24, 2003.

(60) Provisional application No. 60/367,883, filed on Mar. 24, 2002.

(51) Int. Cl.
*G01N 33/53* (2006.01)
(52) U.S. Cl. .................. 436/518; 436/514; 436/807; 436/808; 436/810; 435/287.1; 435/287.7; 435/970; 422/58; 422/61
(58) Field of Classification Search ............. 435/287.1, 435/287.7, 970; 436/514, 518, 807, 808, 436/810
See application file for complete search history.

(56) References Cited

U.S. PATENT DOCUMENTS

| | | | | |
|---|---|---|---|---|
| 4,826,759 A | * | 5/1989 | Guire et al. ............ | 435/4 |
| 5,030,555 A | * | 7/1991 | Clemmons ............. | 435/5 |
| 5,240,917 A | | 8/1993 | Keimowitz et al. .... | 514/159 |
| 2003/0124615 A1 | | 7/2003 | Ens .................... | 435/7.1 |

FOREIGN PATENT DOCUMENTS

| | | |
|---|---|---|
| JP | 01013459 | 1/1989 |
| WO | 01 31052 A1 | 5/2001 |

OTHER PUBLICATIONS

Eikelboom et al., "Aspirin-Resistant Thromboxane Biosynthesis and the Risk of Myocardial Infarction, Stroke, or Cardiovascular Death in Patients at High Risk for Cardiovascular Events", Circulation 105:1650-1655, 2002.
Database Internet 'Online! 2003 Cayman Chemical Inc: "519501 11 dehydro thromboxane assay" retrieved from www.cayrnanchem.com XP002262581 abstract.
Hayashi et al., "Enzyme Immunoassay of Thromboxane $B_2$", Biochimica et Biophysica Acta 750:322-329, 1983, XP009020472.

(Continued)

*Primary Examiner*—Bao-Thuy L Nguyen
(74) *Attorney, Agent, or Firm*—Occhiuti Rohlicek & Tsao LLP

(57) ABSTRACT

A novel method for detecting the concentration of a metabolite in a fluid sample is provided. Devices for the detection of the analyte are also provided. In particular, a device for determining the concentration of 11-dehydro thromboxane in a urine sample and comparing it to a set of standardized quartile concentrations is provided. A concentration of urinary 11-dehydro thromboxane that falls within the fourth quartile is indicative of a greatly increased risk of a recurrent cardiovascular event.

9 Claims, 4 Drawing Sheets

OTHER PUBLICATIONS

Reinke et al, "Development of an Enzyme-Linked Immunosorbent Assay of Thromboxane $B_2$ Using a Monoclonal Antibody", Prostaglandins 37:577-586, 1989, XP009020476.

Cipollone, F., et al. Oxidant stress and asprin-insensitive thromboxane biosynthesis in severe unstable angina. Circulation 2000; 120:1007-1013.

Encyclopedia of Biostatistics, Armitage & Colton, Eds. (1998) (relevant portions attached).

Strongin W. Sensitivity, specificity, and predictive value of diagnostic tests: definitions and clinical applications. Laboratory Disgnosis of Viral Infections, pp. 211-219, 2d. Ed. (1992).

Cipollone, F. et al. Differential suppression of thromboxane biosynthesis by indobufen and aspirin in patients with unstable angina. Circulation 1997;96 1109-1116.

* cited by examiner

DEVICE FOR MEASURING AN ANALYTE

RELATED APPLICATIONS

This application is a continuation-in-part of application No. PCT/CA03/00422 filed on Mar. 24, 2003 which claims priority under 35 USC § 119(e) to U.S. Provisional Application No. 60/367,883 filed Mar. 24, 2002, the entire contents of which are hereby incorporated by reference in their entirety.

FIELD OF THE INVENTION

The present invention relates to the rapid detection of an analyte in a biological sample. Particularly the invention relates to methods and devices for the measurement of suppression of thromboxane generation in response to treatment with aspirin.

BACKGROUND OF THE INVENTION

Cardiovascular disease ranks as a leading cause of mortality and morbidity and represents a significant drain on health resources in many countries.

It is well established that aspirin therapy reduces the risk of a stroke and a first heart attack in healthy individuals, and subsequent heart attacks, strokes, or cardiovascular death in patients with established cardiovascular disease. For example, U.S. Pat. No. 5,240,917 relates to the percutaneous administration of aspirin as an antithrombotic agent.

Studies have shown that aspirin reduces the risk of cardiovascular events by as much as 25% in patients with arterial vascular disease. Most heart attacks and strokes are caused by blood clots in the heart or brain arteries that form on top of cracked atherosclerotic plaques. These blood clots are predominantly composed of clumped platelets. Aspirin works to prevent blood clot formation at these sites by reducing the ability of the platelets to clump together and form platelet aggregates. Aspirin, also known as acetylsalicylic acid, reduces platelet reactivity because its acetyl group acetylates a key intra-platelet enzyme known as cyclo-oxygenase. Once acetylated, cyclo-oxygenase cannot work to generate thromboxane A2, a substance released from the platelets that serves to activate other platelets and induce them to clump together in aggregates. In order for aspirin to work, therefore, it must reduce thromboxane A2 levels.

Thromboxane A2 has a very short half-life, and is rapidly converted to a stable metabolite called thromboxane B2. Although thromboxane B2 can be measured in blood, the tests can be problematic because platelets can be activated during the collection process. Once activated, the platelets will release thromboxanes that can interfere with the assay. It is therefore preferable to measure thromboxane B2 in the urine.

Even though platelets are an important part of blood clots, rapid technology to measure and predict platelet physiology is lacking. Some accepted laboratory methods include:
  i) Bleeding Time, a test which is qualitative, not quantitative;
  ii) Platelet Aggregometry. This test measures the clumping of platelets in response to various stimuli. The test is arduous, time-consuming, and expensive and is not specific for the effects of aspirin on platelet activation; and
  iii) Tests of platelet activation using fluorescent cell sorting techniques. This test can only be done on freshly collected blood and uses size separation to separate platelets from other blood cells and fluorescently-tagged antibodies to identify activated platelets. This test is cumbersome and does not provide aspirin-specific information.

The present invention provides a novel method for assessing platelet function and correlating a readout of that function with the risk of a cardiovascular event.

Aspirin is effective for patients with heart attacks, strokes or peripheral arterial disease or those at risk of these disorders. Aspirin has also been shown to be effective in reducing the incidence of pregnancy-induced hypertension and pre-eclamptic toxicity in women at risk. A role for aspirin in reducing the risk of fatal colon cancer has also been suggested and aspirin may be useful in the treatment of patients with antiphospholipid antibodies, including the lupus anticoagulant. Thus, determining the effectiveness of aspirin treatment in many conditions is an important prognostic factor and may help physicians recommend the most appropriate therapeutic course.

While aspirin is effective in many individuals, approximately 10 to 20% of patients with arterial thrombosis who are treated with aspirin have a recurrent vascular event during long-term follow-up. The failure of these patients to derive a beneficial effect from aspirin is termed "aspirin resistance". There are several possible explanations for aspirin resistance but, whatever the underlying cause, the result is the same. It would obviously be beneficial to be able to identify those patients who are aspirin resistant in order to help physicians determine the advisability of altering the aspirin dose or administering alternative or additional anti-platelet therapies. A need therefore exists for a simple method to accurately determine the response to aspirin and predict the likelihood of onset of a cardiovascular event or other medical condition that would benefit from lowering of thromboxane-A2 levels.

SUMMARY OF THE INVENTION

To be able to identify those people at particular risk of having a recurrent vascular event, so that they can be appropriately treated before a heart attack or stroke occurs, would be of great clinical importance. Former attempts to develop predictive assays, particularly those utilizing blood, have had mixed results. Thus, it is an object of one aspect of the present invention to provide a rapid, non-invasive, reproducible method for determining aspirin resistance. The present invention demonstrates for the first time an association between aspirin resistance, defined as failure of suppression of thromboxane generation, and cardiovascular risk. Determination of the degree of resistance to aspirin is used to predict the risk of a cardiovascular event or other condition that would benefit from lowering thromboxane A2 levels.

The present invention is based on the observation that urinary thromboxane A2 metabolite levels in patients are a surprisingly accurate predictor of recurrent cardiovascular mortality. Thus, determination of metabolite levels in patients may serve to identify those patients at particular risk of developing cardiac ischemia or stroke.

In one aspect of the invention, a method for assessing aspirin resistance in a patient is provided. The method comprises determining the concentration of a metabolite of thromboxane A2 in a sample of body fluid from the patient. The method preferably further comprises the step of comparing the concentration of metabolite in the sample to a predetermined set of concentration quartiles to determine within which quartile the sample falls and determining aspirin resistance based on the quartile of the sample. A concentration of metabolite within the second, third or fourth quartile is indicative of an increased risk of a cardiovascular event.

In another aspect, a method for assessing the risk of a cardiovascular event in a patient is provided. The method comprises determining the level of thromboxane B2 or another thromboxane A2 metabolite in a body fluid, preferably urine. In a preferred embodiment, the method comprises an immunoassay in which a body fluid sample from the patient is contacted with an antibody that specifically binds to a metabolite of thromboxane-A2. The formation of immune complexes is then detected to determine the level of antigen in the sample and the sample level thus obtained is compared to control levels to determine a relative risk factor.

In another aspect, there is provided a method of screening a patient for risk of having a cardiovascular event which comprises contacting a body fluid sample from the patient with an antibody which specifically binds to a thromboxane-A2 metabolite, determining the degree of immune complex formation by immunoassay, and assessing the patient's risk of a cardiovascular event upon the basis of immune complex formation.

In a preferred embodiment, the patient has arterial vascular disease and the method is used to predict the risk of a recurrent vascular event.

In a further preferred embodiment, the metabolite that is measured is thromboxane-B2 metabolite, preferably 11-dehydro thromboxane B2.

In a further aspect, a urine level of this metabolite of greater than 15 ng/mmol creatinine is indicative of risk of a cardiovascular event, more preferably a urine level greater than 21.9 ng/mmol creatinine is indicative of risk of a cardiovascular event and most preferably a urine level greater than 33.8 ng/mmol creatinine is indicative of risk of a cardiovascular event.

The present invention also provides a kit for assessing aspirin resistance. The kit typically comprises (a) an antibody that specifically binds to a thromboxane A2 metabolite, and (b) a labeled sample of the metabolite.

In another aspect of the invention, a device for detecting an analyte in a test sample obtained from a mammal is provided. The device comprises an immobilized moiety that specifically binds to the analyte and means for visually determining the level of the analyte. The moiety that specifically binds the analyte is preferably an antibody, an antibody fragment, a single chain antibody or an antigen-binding domain of an antibody. The binding moiety is immobilized on a solid support selected from the group consisting of glass, polystyrene, nylon, cellulose acetate, nitrocellulose and other polymers. The device may be in the format of a dipstick. In a preferred embodiment, the analyte is 11-dehydro thromboxane B2.

In yet another aspect of the invention a method of predicting increased risk of an increased risk for a recurrent cardiovascular event is provided. The method comprises:
 a) measuring the concentration of 11-dehydro thromboxane B2 in a test urine sample;
 b) comparing the concentration of the test sample to the quartile concentration of a series of reference samples;
 c) determining which quartile concentration the test sample falls within; and
 d) predicting the risk based on the corresponding quartile concentration.

In a particularly preferred embodiment, an immunoassay device for detecting the presence of an analyte is provided. The device comprises a strip that comprises a reagent that specifically binds to the analyte to be tested. The reagent is preferably distributed in patches to detect different amounts of the analyte.

In another embodiment, an immunoassay device is provided which comprises two strips that are reversibly attached. One strip comprises an absorbent material capable of absorbing a predetermined volume of urine or other bodily fluid and the second strip comprises patches having different amounts of a moiety that specifically binds the analytes to be tested.

In yet another embodiment, an immunoassay device is provided comprising a first strip having an antibody moiety which specifically binds the analyte to be determined and a second strip containing at least one standardized concentration of the analyte to be determined, wherein upon addition of a test sample, analyte in the test sample competes with analyte on the second strip for binding by the antibody moiety.

The present invention provides a device for detecting an analyte in a test sample obtained from a mammal. The device comprises at least one assay strip having a plurality of patch regions, each patch region containing a unique, predetermined amount of a recognition molecule specific for the analyte. Interaction between the analyte and the recognition molecule provides a dose dependent colorimetric readout on the patch regions. Preferably, the recognition molecule is selected from the group consisting of an antibody, an antibody fragment, a single chain antibody, an antigen binding domain of an antibody, a ligand or a receptor. The analyte is preferably 11-dihydro thromboxane B2.

In another embodiment, the device comprises a first assay strip comprising an absorbent material capable of absorbing a predetermined amount of fluid and a second non-absorbent assay strip comprising a specific recognition molecule. The presence of an analyte in the absorbed fluid can be detected by allowing the first strip to interface with the second strip and determining the amount of recognition molecule bound to the analyte. Upon interaction of the first and second strip, the recognition molecule migrates from the second strip to the first strip and the amount of antibody remaining on the second strip is indicative of the concentration of analyte in the sample. The recognition molecule is preferably an antibody and the analyte is a thromboxane metabolite.

In yet another embodiment a device for the detection of an analyte is provided. The device comprises a first strip of absorbent material having a recognition molecule dispersed therein and a second non-absorbent strip have predetermined amounts of an analyte standard immobilized thereon, wherein upon immersion of the device in a sample fluid the recognition molecules are mobilized to competitively bind to the analyte on the second strip or the analyte in the sample fluid whereby the amount of recognition molecule bound to the second strip is inversely proportional to the concentration of analyte in the sample fluid.

An immunoassay system for the detection of thromboxane B2 is provided which comprises:
 a) a first strip having an antibody specific for thromboxane B2, and
 b) a second strip impregnated with a labeled standard concentration of thromboxane B2,
 wherein upon exposure of the device to a test sample, thromboxane B2 in the test sample competes with the impregnated thromboxane B2 for binding to the antibody specific for B2 and the level of thromboxane B2 in the sample is inversely proportional to the amount of labeled thromboxane B2 remaining on the second strip.

The methods and devices of the present invention can proactively identify patients who are relatively resistant to anti-thrombotic doses of aspirin and who may benefit from higher doses of aspirin or additional or alternative therapies that can either block thromboxane production or activity or inhibit another pathway of platelet activation.

DETAILED DESCRIPTION OF THE INVENTION

Figure 1:
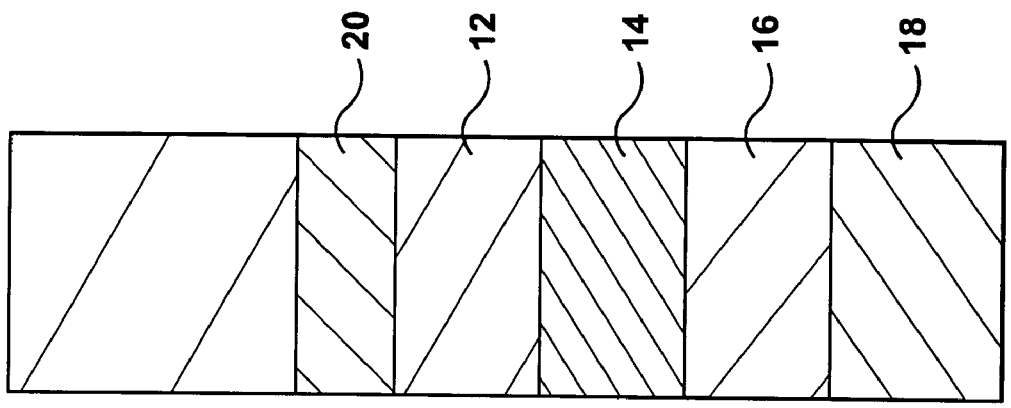
FIG. 1 demonstrates graphically the relationship between 11-dehydro thromboxane B2 levels and risk of a cardiovascular event.

Survivors of acute myocardial infarction are at greatly increased risk for subsequent fatal and non-fatal cardiovascular events. This heightened risk is influenced by many factors, such as age, co-morbid diseases and response to treatment.

The term "cardiovascular event(s) as used herein refers to coronary and/or cerebrovascular event(s) including primary myocardial infarction, secondary myocardial infarction, angina pectoris (including unstable angina), congestive heart failure, sudden cardiac death, cerebral infarction, syncope, transient ischemic attack and the like.

While aspirin has been known to reduce thromboxane-A2 levels, the present invention provides a novel method for determining aspirin resistance. The degree of aspirin resistance can be used to predict the occurrence of a cardiovascular event based on the surprising result that there is a correlation between the level of 11-dehydro thromboxane B2 and the incidence of myocardial infarction, stroke and cardiovascular death.

The present invention provides a method for determining the risk of a recurrent cardiovascular event based on the level of thromboxane-A2 produced in response to treatment with aspirin. The level of thromboxane-A2 generation can be determined by measuring urinary levels of metabolites of thromboxane-A2. A preferred stable metabolite of thromboxane-A2 which can be measured is 11-dehydro thromboxane B2.

In responsive individuals, aspirin reduces levels of thromboxane A2 by irreversibly acetylating the enzyme, cyclo-oxygenase 1. However, a subpopulation of individuals does not exhibit this inhibition of thromboxane generation in response to aspirin. The incomplete suppression of thromboxane generation with the usual dose (75 to 325 mg/d) of aspirin is termed aspirin resistance. In patients with cardiovascular disease taking aspirin, those who are aspirin resistant are more likely to have a recurrence of a cardiovascular event. The present invention provides a method for identifying those patients who are aspirin resistant. In addition to the prediction of a cardiovascular event, aspirin resistance may be an important factor in the selection of a treatment for other conditions that would benefit from a lowering of thromboxane levels.

The present invention provides a method of determining the progression of a disease associated with resistance to aspirin. Individuals with a higher aspirin resistance status tend to resist treatment with aspirin and tend to have a greater incidence of conditions associated with uninhibited thromboxane 2 levels.

The present invention provides a method for establishing quartiles of thromboxane B2 levels and correlating those quartile levels with risk of a cardiovascular event. Based on the range of levels found in patients treated with aspirin, four quartiles were established. The first quartile comprised levels less than 15.1 pg/mmol creatinine. The second quartile comprises levels between 15.1 to 21.8 pg/mmol creatinine. The third quartile comprises levels between 21.9 and 33.8 pg/mmol creatinine and the fourth quartile comprises levels greater than 33.8 pg/mmol. It is clearly apparent that these ranges are approximate and that in any study the quartile ranges may vary. The odds ratio for an incidence of a cardiovascular event over a five year period are 1.0, 1.3, 1.4, and 1.8 for the first to fourth quartiles, respectively. Thus, the risk of having a cardiovascular event over a study period of approximately 5 years is 80% greater for those in the fourth quartile as opposed to those in the first quartile.

The method for assessing the risk of a cardiovascular event comprises measuring thromboxane B2 levels in urine and determining which quartile the level falls within. The association of a test level within a quartile range is indicative of the long-term relative risk of myocardial infarction, stroke and vascular death. Urinary levels of 11 dehydro thromboxane B2 that are predictive of future cardiovascular events are generally greater than 15 pg/mmol of creatinine. Urinary 11-dehydro thromboxane levels that are predictive of cardiovascular events are preferably in a range of about 15 to 100 pg/mmol creatinine, more preferably 21 to 100 pg/mmol creatinine and most preferably in a range of 30 to 100 pg/mmol creatinine.

FIG. 1 illustrates the association between quartiles of 11-dehydro thromboxane B2 levels and composites of myocardial infarction (MI), stroke, or cardiovascular (CV) death that was seen in an exemplary study. The study on which these results are based is discussed in further detail in Example 1 below. The results indicate that if the test value falls within the first quartile, there is an absolute risk of approximately 10%. If the test value falls within the second quartile, there is an absolute risk of about 13% over 5 years. If the test value fall within the third quartile, the absolute risk is about 14% and if the value falls within the fourth quartile, the risk is about 18%.

The present invention provides a method of predicting the occurrence of a cardiovascular event in a patient, wherein a body fluid of the patient is subjected in vitro to determination of the levels therein of a thromboxane-A2 metabolite or a fragment thereof.

The invention also provides a method of screening patients, for risk of having a cardiovascular event or other condition which would benefit from the reduction of thromboxane A2 levels, wherein a body fluid of the patient is subjected in vitro to determination of the levels therein of a thromboxane A2 metabolite or a fragment thereof and an assessment of the patient's risk is made upon the basis of those levels.

Such screening may be positive i.e. to identify those patients at risk and consequently in need of alternative treatment or negative to eliminate those patients who are not at significant risk from extensive follow-up.

Various methods can be used to measure the level of thromboxane-A2 metabolites in a sample of biological fluid. The level can be measured using a method selected from the group consisting of chromatography, immunoassay, spectroscopy and other quantitative methods known to those skilled in the art. The chromatographic method is preferably high performance liquid chromatography (HPLC) or gas chromatography (GC). The spectroscopic method is preferably selected from the group consisting of ultraviolet spectroscopy, infrared spectroscopy and nuclear magnetic resonance spectroscopy.

Various types of immunoassays can be used. For example, a "sandwich" assay in which the metabolite is sandwiched between a capture antibody immobilized on a solid support and a detecting labeled can be used to determine the amount of bound labeled antigen antibody complex. Alternatively a competition immunoassay may be used in which an antibody is bound to a support which is contacted with an unknown quantity of sample metabolite and labeled antigen of the same type. The amount of labeled antigen bound to the support is indicative of the amount of antigen in the sample.

The term "antibody" is used herein to refer to a monoclonal or polyclonal antibody or an antibody fragment having specific binding affinity. The term "antibody fragment" refers to a portion of an antibody, such as an antigen binding domain, a hypervariable domain of either the heavy or light chain and the term also includes single chain antibodies.

Some examples of solid supports that can be used in the present invention include plates, tubes, polystyrene beads, nylon, nitrocellulose, cellulose acetate, glass fibers and other types of porous polymers.

The methods of the present invention can be performed using immunoassay kits. The kits may be dip-stick, flow-through or migratory in design as well as other formats known to those skilled in the art.

The immunoassay determination of thromboxane A2 metabolites can be performed using monoclonal or polyclonal antibodies, which may be raised using techniques conventional in the art. For example, antibodies may be made by injecting a host animal, e.g. a mouse or rabbit, with the antigen. The antigen may be conjugated with an immunogenic protein such as PPD, a protein derivative of tuberculin, Keyhole Limpet Haemocyanin, BSA etc., to provide either a serum containing polyclonal antibodies or spleen cells for fusion to provide hybridomas or immortalised cell lines. Other standard methods may also be used.

In a preferred embodiment, the immunoassay comprises the use of an antibody in immobilised form, e.g. on microtitre plates, membranes or beads, to trap the antigen. In a sandwich assay, the bound antigen may be labeled using additional soluble antibody, which may be monoclonal or polyclonal and which may either carry a label or, more conveniently, may itself be labeled subsequently by reaction with a secondary antibody carrying a label.

Suitable labels include radionucleides, fluorophores, chemiluminescent labels, bioluminescent labels, enzymes, for example as used in ELISA systems, dyes or particles such as colloidal gold. The assay for determining the concentration can be in the format of an RIA, ELISA, immunofluorometric assay or immunoradiometric assay.

Alternatively, a competitive binding assay may be used, wherein a known quantity of labeled metabolite is added to the analyte solution and contacted with a limited quantity of the immobilised monoclonal antibody, whereby the amount of labeled antigen which is immobilised is inversely proportional to the amount of target antigen present in the analyte.

In one aspect of the invention, a method for determining aspirin resistance is provided. The method comprises:
  a) contacting a body fluid with an antibody reactive with 11-dehydro thromboxane for a time and under conditions sufficient to form an antigen-antibody complex and detecting the antigen-antibody complex formed;
  b) quantitating the amount of complex formed in step a); and
  c) comparing the amount of complex quantitated in step b) with standard concentrations, wherein an elevated level of 11-dehydro thromboxane correlates with aspirin resistance.

In a preferred embodiment, the method further comprises quantitating the degree of aspirin resistance to predict the risk of a cardiovascular event.

In another aspect of the invention, the components needed to perform the immunoassay are supplied in kit form. Such a kit would comprise:
  (a) an antibody capable of binding to 11-dehydro thromboxane A2, the antibody in an immobilised form;
  (b) a control preparation of 11 dehydro thromboxane B2; and
  (c) a labelled secondary antibody specific for 11 dehydro thromboxane B2.

In a preferred embodiment of the method of the invention, a quantitative determination of 11 dehydro thromboxane B2 levels in urine may be obtained, wherein a level greater than 15 ng/mmol creatinine is indicative of an increased risk of heart failure.

The body fluid on which the determination is performed may be any body fluid in which 11 dehydro thromboxane may be located. It is preferably urine. In some cases it may be convenient to extract the peptide, or otherwise treat the sample prior to determination.

Because 11-dehydro thromboxane B2 is highly stable on storage, a reliable prognosis may be obtained when the determination is performed on samples that have been stored for some time. This is advantageous in that it facilitates assay reproducibility and it enables the assay to be delayed post sample collection. Another advantage of the method of the invention is that the 11 dehydro thromboxane B2 determination can be performed with high specificity and sensitivity leading to an accurate and reliable prediction of recurrent cardiovascular events. Prior art methods do not approach this level of accuracy and sensitivity.

Figure 2:
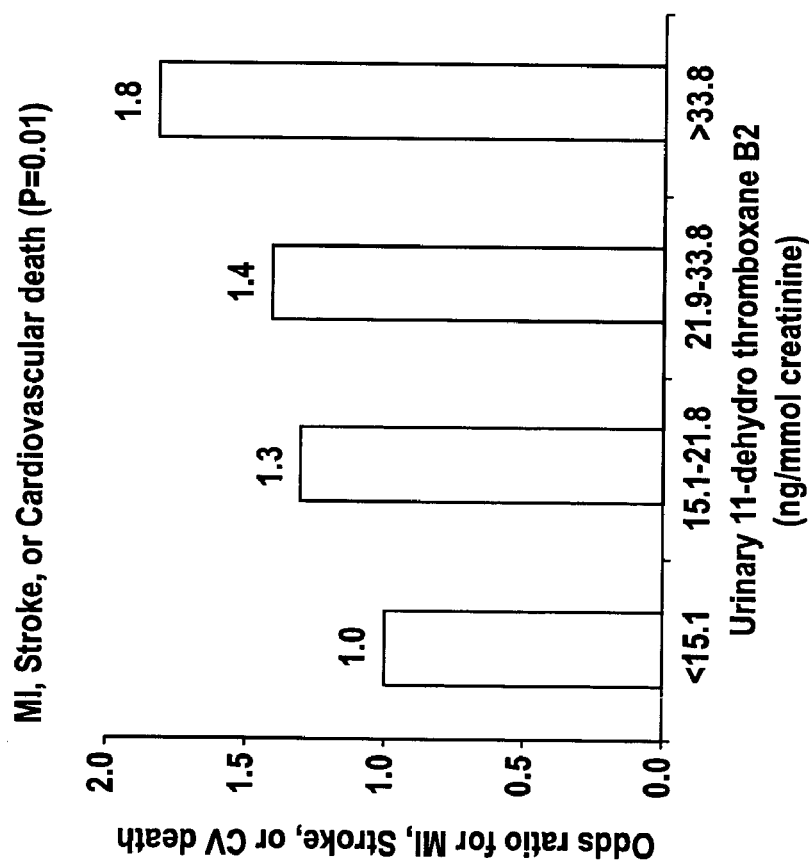
FIG. 2 illustrates one embodiment of a test device according to the present invention.

The present invention provides a novel test kit or device for the measurement of an analyte. The devices of the present invention may also be referred to as immunoassay systems. One preferred embodiment of a device for the determination of analyte levels is shown in FIG. 2. Although thromboxane is referred to herein as an example of analyte that can be detected using the novel assay devices of the present invention, it is clearly apparent that the devices described herein can also be used to detect other analytes by using different reagents on the device. A test strip 10 is provided which is divided into test patches, 12, 14, 16 and 18. Each patch has a reagent that reacts to the presence of 11-dehydro thromboxane B2 or any other analyte to be detected. Each reagent is applied so it will react with a predetermined concentration of the analyte, e.g.11-dehydro thromboxane B2, in a given amount of time. In a particularly preferred embodiment, each of the said patches, 12, 14, 16 and 18 are adjusted to react to concentration of 11-dehydro thromboxane B2 in urine of a) less than 15.1, b) 15.1 to 21.8, c) 21.9 to 33.8 and d) greater than 33.8 (expressed as ng/mmol creatinine), respectively. In other embodiments, the patches are adjusted to react to various concentrations of other analytes. The device is processed so a dye or other calorimetric agent provides a readout of the level 11-dehydro thromboxane B2 present in the urine. Various colorimetric agents can be used and the processing steps required for their detection will vary according to the agents. Methods for the detection of colorimetric agents in immunoassays are well known to those skilled in the art. The test strip 10 may also include a patch 20 that changes color when the patch has been in the urine or other fluid for an appropriate amount of time to obtain the desired reaction. The reagents used for this patch 20 would react to known substances in the urine or other fluids. In some preferred embodiments the patches 12, 14, 16, 18 also have printed on each of them the absolute and relative risk factors associated with the amount of 11-dehydro thromboxane B2 detected on that particular patch. This would allow the clinician to directly obtain the risk to the patient tested from the test strip itself. This would speed diagnosis and avoid errors.

Figure 3:
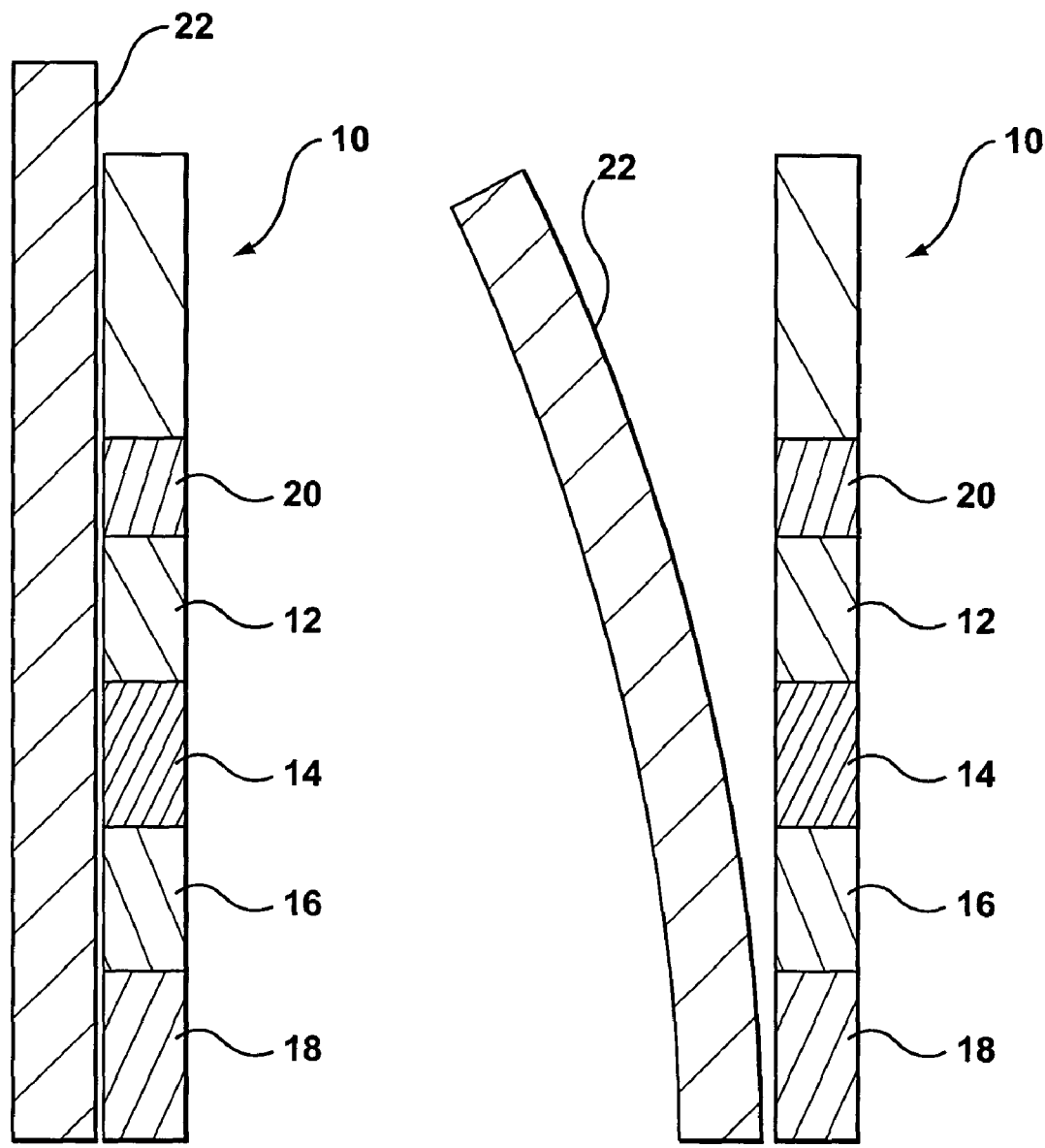
FIG. 3 illustrates the test device of FIG. 2 in association with a second strip.

In a preferred embodiment shown in FIG. 3, the test strip 10 is releasably attached to a second strip 22. The second strip 22 is typically made of an absorbent material and can absorb a predetermined amount of urine. When the two strips are in contact with each other, the moieties on the two strips can interact to produce a signal. Typically an antibody, or other recognition molecule will react with an analyte contained in the urine absorbedonto the second strip. This test device can be used to detect the presence of and/or quantitate the amount of an analyte in a sample. The sample may be urine, as mentioned above, or it may be another fluid.

Figure 4:
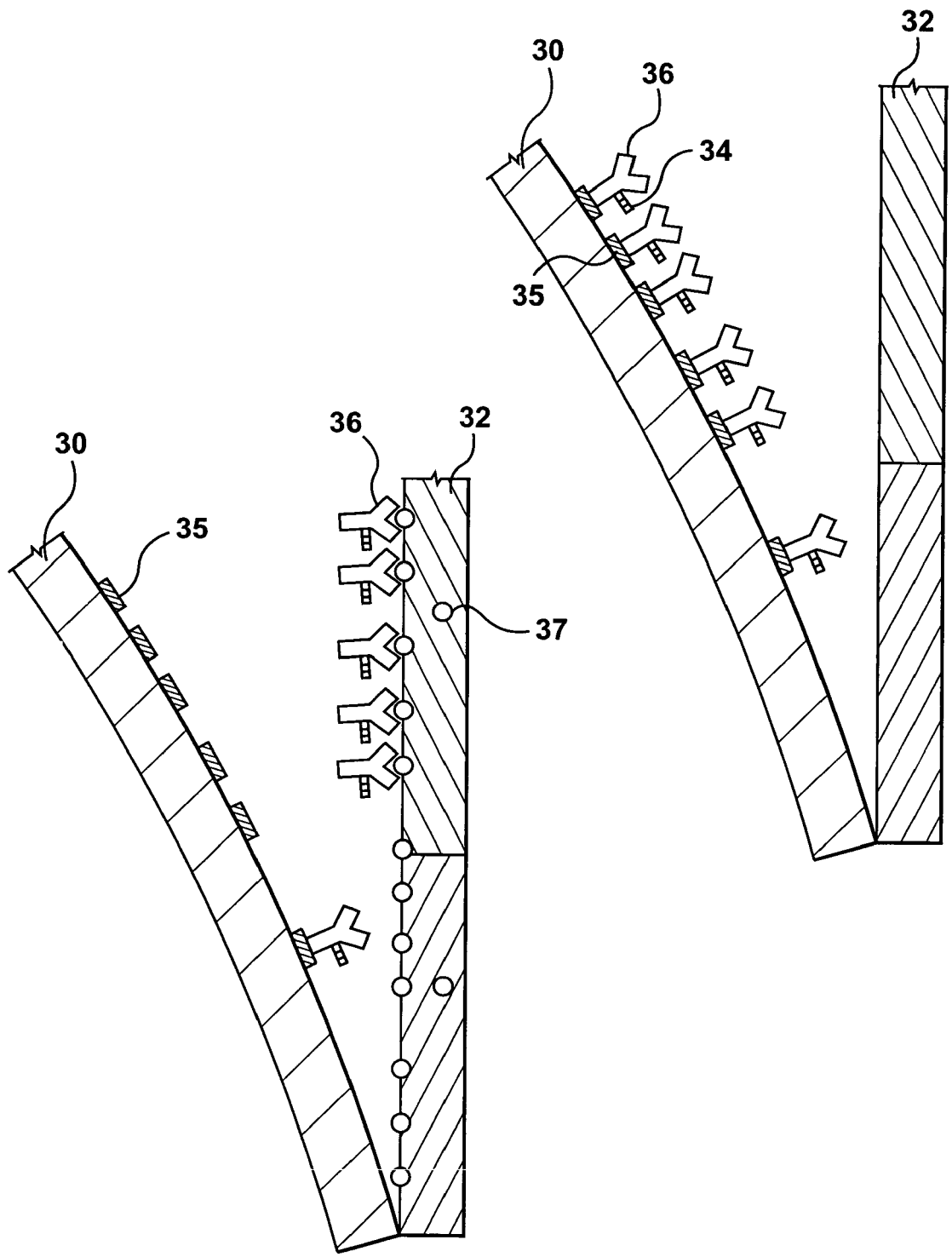
FIG. 4 illustrates a preferred embodiment of a test device of the present invention.

One preferred device according to the present invention is shown in FIG. 4. This system includes two strips 30, 32 which are detachably joined so that they can be immersed into the urine sample while bonded together, but can then be pulled or peeled apart at the appropriate time when the user wishes to view the results of the reactions. In one preferred embodiment of the invention, strip 32 is made of an absorbent material, such as a porous micro filter polymer membrane or similar material designed to absorb a fixed volume of urine when the two strips are immersed in the urine sample. The other strip 30 comprises a polymer membrane or sheet made, for example, of nitrous cellulose or similar material. This membrane is preferably impregnated with or coated with a fixed concentration of a reporter molecule 34 such as a dye or enzyme that is linked to an antibody or other bioreceptor 36 specific for the analyte to be detected, such as 11-dehydro thromboxane B2. Strip 30 is made of a material that does not allow urine to be absorbed into it, preferably a hydrophobic material. The interface between strip 30 and strip 32 allows the 11-dehydro thromboxane B2 contained in the urine in strip 32 to come in contact with the antibody specific for 11-dehydro thromboxane B2 contained in and/or on strip 30. Movement of labeled antibody between strips 30 and 32 may be facilitated by providing, between the antibody and strip 30, a separable physical bond 35 in a manner that retains adequate analyte recognition between the antibody and the 11-dehydro thromboxane B2 associated with the strip. The bond may be accomplished using IgG Fc region specific binding proteins such as Protein A, Protein G, or secondary antibodies specific for the Fc region of the primary antibody. This separable physical bond provides a means of anchoring the antibody 36 to strip 30. After being immersed in the urine, the two strips are incubated for a fixed time period and then separated. The antibody 36 is capable of recognizing the analyte 37 present in the urine and will migrate to the strip 32. The present invention takes advantage of the affinity between the antibody and the analyte, e.g. 11-dehydro thromboxane B2. In a preferred embodiment, the antibody remains on strip 30 if it does not react with 11-dehydro thromboxane B2 in the urine. If the antibody binds to 11-dehydro thromboxane B2 contained in the urine on strip 32 it will be removed from strip 30. A signalling moiety is associated with the antibody and thus, after processing of the strips, the amount of signal on strip 30 is inversely proportional to the amount of 11-dehydro thromboxane B2 contained in the urine when the two strips 30 and 32 are peeled apart. The strip optionally comprises at least two, preferably 4, reference patches that allow comparison between the level of signal resulting from the reaction and the visual signal that corresponds to each of the four levels of 11-dehydro thromboxane B2 (less than 15.1, 15.1 to 21.8, 21.9 to 33.7 and finally greater than 33.7 referred to above).

This system may also indicate the corresponding risk levels that correspond to the amounts of 11-dehydro thromboxane B2 contained in the urine. The concentrations of antibody can be altered to provide optimal signal to noise ratios. The device shown in FIG. 4 can also be modified for the detection of other analytes by using different recognition molecules. In addition the test sample may comprise a fluid other than urine.

Figure 5:
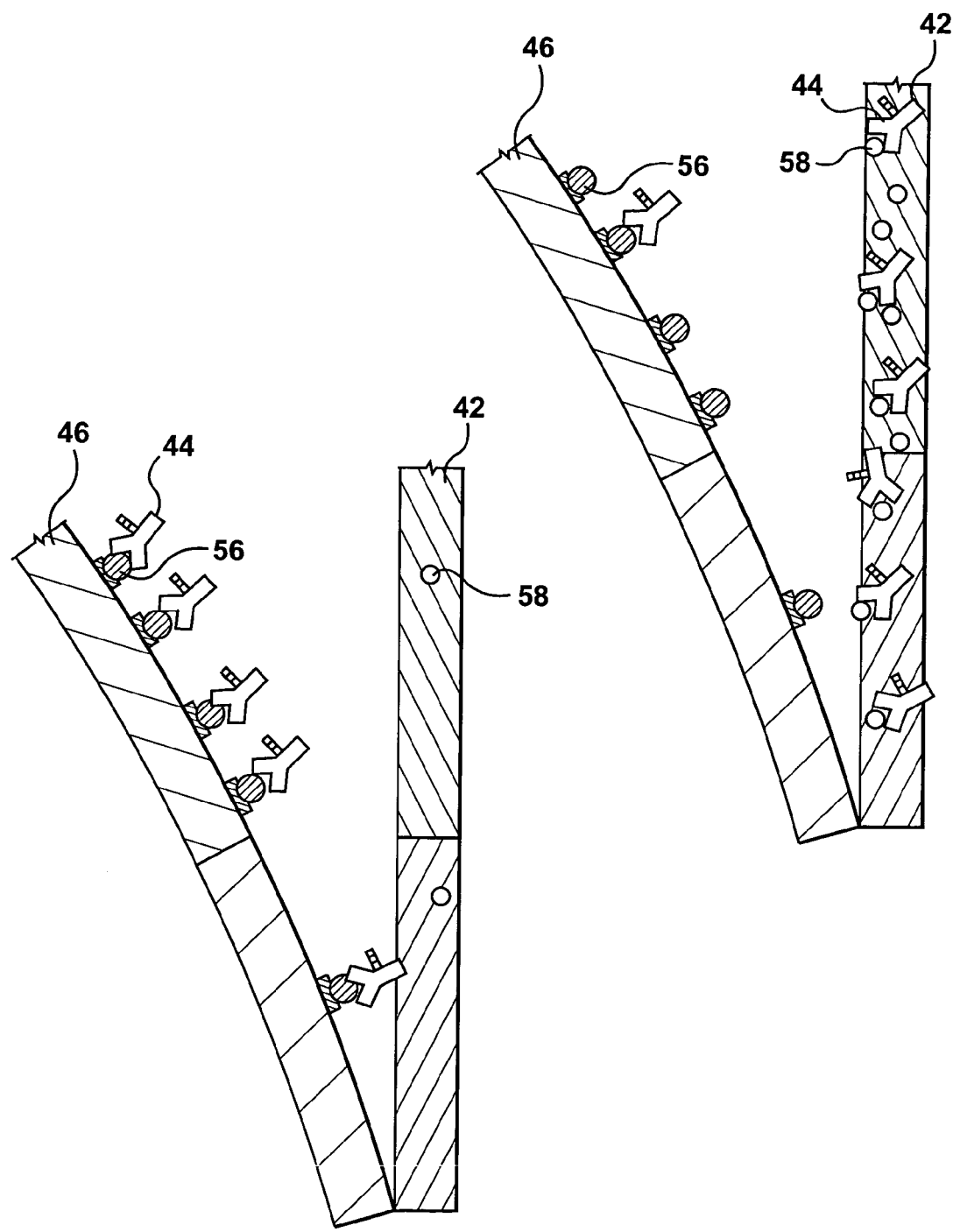
FIG. 5 illustrates yet another embodiment of a test device.

In another embodiment, shown in FIG. 5, strip 42 has a labeled antibody 44 associated with it. Partner strip 46 may optionally comprise at least two, preferably four, patches 48, 50 which contain increasing densities of synthetic or natural analyte (e.g. 11-dehydro thromboxane $B_2$) 56 immobilized to the surface. When the device is immersed in the urine sample, the labeled antibody is mobilized to distribute itself between the analyte in the sample 58 and the immobilized analyte 56 on strip 44. In other words, there is competitive binding between the analyte in the urine on one strip and the immobilized analyte on the partner strip. The presence of analyte in the urine sample blocks binding of the labeled antibody to the immobilized analyte on the patches in a dose-dependent manner. The analyte is detected and quantified by the relative binding to the patches of increasing density.

While preferred embodiments comprising two strips of material have been described, it should be understood that these components could be segments of a larger belts or rollers. It is also clearly apparent that either a positive (increase in signal intensity) or a negative (decrease in signal) readout can be used on either strip as an indicator of the amount of analyte in the test sample. The devices of the present invention can be used to detect the presence of virtually any analyte in a fluid sample as long as there is a recognition molecule specific for that analyte. It is also apparent that while the devices of the present invention have been described with the example of determining quartile concentrations of thromboxane, the strips do not have to be limited to quartile determinations. The reagents on the strips of the invention can be selected for other types of concentration determinations. For example, the strips can be designed to detect only concentrations in excess of a predetermined threshold amount or the absolute concentration of an analyte can be determined. The single and dual strip devices described herein offer significant advantages over other immunoassay methods. Only a small volume of test sample is required and a clinically relevant readout can be quickly and easily obtained.

While the present invention has been described in conjunction with preferred embodiments, the measurement of analyte or simultaneous measurement of two or more analytes (such as 11-dehydro thromboxane $B_2$ and creatinine) can also be performed using existing rapid testing technologies such as, but not limited to biosensors or membrane based dipstick, lateral flow or chromatographic strips.

While these embodiments have described a method for analyzing the amount of 11-dehydro thromboxane $B_2$ in a test sample, it should be understood that in other embodiments of this invention, other thromboxane A2 metabolites can be measured as an indicator of aspirin resistance. It is apparent that for the detection of other metabolites, other antibodies that have an affinity for those metabolites will be substituted for the purpose of analyzing the presence and amount of these other proteins.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

As will be demonstrated in the examples to follow, the early detection of aspirin resistance is an important indicator for improved long-term overall survival and reduced mortality and morbidity due to major cardiovascular events. In particular, 11-dehydro thromboxane levels of greater than 33.8 pg/mmol creatinine are associated with an 80% greater risk of a cardiovascular event than levels less than 15.2 pg/mmol creatinine. By recognizing aspirin resistance and its implications, overall deaths can be reduced and congestive heart failure requiring hospitalization can be reduced. The detection of aspiring resistance is also important for the development of an appropriate treatment strategy for other condition which may benefit from a reduction thromboxane A2 levels.

EXAMPLES

The examples are described for the purposes of illustration and are not intended to limit the scope of the invention.

Example 1

Study Design

The HOPE study[1] was an international, randomised, placebo-controlled, two-by-two factorial trial of ramipril and vitamin E for the secondary prevention of cardiovascular disease. The institutional review committee at each participating center approved the study and all subjects gave informed consent.

Patients

A total of 9,541 patients aged at least 55 years at the time of randomization who had a history of coronary artery disease, stroke, peripheral vascular disease, or diabetes plus at least one other cardiovascular risk factor were assigned to one of four treatments: ramipril titrated up to 10 mg daily, vitamin E 400 IU daily, both, or neither. The study commenced in December 1993 and was terminated prematurely on Mar. 22, 1999 because of clear evidence of a benefit of ramipril.

Urine Sample Collection

All study participants were asked to provide a first morning urine specimen at the time of randomisation. Of the 9,541 patients in the HOPE study, 9,282 (97%) provided baseline urine samples. Samples (n=5529) from the 129 Canadian centres participating in this study were sent to the central laboratory in Hamilton, Canada where they were stored at −80° C. until analysis. Only samples from Canadian centres were used for the present study.

Follow-up and Ascertainment of Clinical Outcomes

All patients in the HOPE study were followed at one month, six months, and six monthly intervals thereafter until completion of the study. At each follow-up, clinical outcomes were recorded and medication use, including aspirin, was documented. The primary outcome was the composite of myocardial infarction, stroke, and death from cardiovascular causes.

Selection of Cases and Controls

Of patients with available urine samples (n=5529), only those who were taking aspirin at the time of commencement of the run-in phase (prior to randomisation), at randomisation (coinciding with the time of urine collection), and at each follow-up visit, were eligible for inclusion. Aspirin-treated patients who provided an adequate baseline sample of urine and had a confirmed myocardial infarction, stroke, or cardiovascular death after randomisation were defined as cases. Controls were randomly selected from aspirin-treated patients who provided an adequate baseline urine sample but did not experience myocardial infarction, stroke, or cardiovascular death after randomisation. Controls were matched according to gender and age (±5 years) in a 1:1 ratio with cases.

Laboratory Analysis

For each case and control, urine collected and stored at baseline was thawed and assayed for 11-dehydro thromboxane $B_2$ levels using a commercially available enzyme immunoassay (Cayman Chemical, Ann Arbor, Mich.) that has inter- and intra-assay coefficients of variation of 12.1% and 10%, respectively. Assays were performed by laboratory staff blinded to patient status as case or control. In addition, case and control specimens were assayed in random order, thereby reducing the possibility of systematic bias.

Statistical Analysis

Means or proportions for baseline demographics and risk factors were calculated for cases and controls. The significance of any difference between cases and controls was tested using Student's paired t-test for means and McNemar chi square test for proportions, which takes into account the matching between cases and controls. Because 11-dehydro thromboxane $B_2$ values are skewed, geometric means were calculated after log transformation of the raw data and the significance of any differences in geometric mean values between cases and controls was tested using Student's paired t-test. Median concentrations also were calculated and levels in cases and controls were compared using Wilcoxon's rank-sum test.

Tests for trend were used to assess any association between increasing baseline urinary 11-dehydro thromboxane $B_2$ concentrations and risk of myocardial infarction, stroke, or cardiovascular death after dividing the samples into quartiles defined by the distribution of the complete cohort. Adjusted estimates of the association between increasing baseline urinary 11-dehydro thromboxane $B_2$ concentrations and risk of myocardial infarction, stroke, or cardiovascular death were obtained using conditional logistic regression modelling that accounted for the matching variables and controlled for the random treatment assignment and baseline differences between cases and controls. A separate multivariable regression model was used to examine the association between baseline patient characteristics, including age, gender, heart rate, blood pressure, body mass index, past history of vascular disease, conventional vascular risk factors, lipid-lowering therapy, beta-blockers, diuretics, and randomised treatment allocation (ramipril or vitamin E), and urinary 11-deydro thromboxane $B_2$ concentrations in the urine.

All P-values are two-sided and confidence intervals are calculated at the 95 percent level.

Baseline characteristics of cases and controls are shown in Table 1. As expected, patients in whom myocardial infarction, stroke, or cardiovascular death subsequently developed had a higher mean body mass index and baseline blood pressure and were more likely than those who remained free of these events to be current smokers or have a history of hypertension, diabetes, myocardial infarction, or peripheral vascular disease. Cases also were more often treated with diuretics or calcium channel blockers at baseline and less often treated with lipid-lowering drugs or randomised to ramipril therapy. Because of the matching, the age and gender of cases and controls were similar.

Geometric mean and median urinary concentrations of 11-dehydro thromboxane $B_2$ at baseline were significantly higher among patients who subsequently developed the composite outcome of myocardial infarction, stroke, or cardiovascular death compared with those who remained free of these events (Table 2). The difference between cases and controls was greatest in those who suffered a myocardial infarct (24.5 vs. 20.9 ng/mmol creatinine, P=0.003) or died from a cardiovascular cause (25.6 vs. 20.4 ng/mmol creatinine, P<0.001).

The adjusted odds for the composite outcome of myocardial infarction, stroke, or cardiovascular death increased with each increasing quartile of baseline urinary 11-dehydro thromboxane $B_2$ concentration (P for trend across quartiles, 0.01), with patients in the highest quartile having a risk 1.8-fold higher than those in the lowest quartile (Odds Ratio [OR] 1.8; 95 percent confidence interval [CI] 1.2-2.9, P=0.009) (FIG. 1). A similar association was seen with myocardial infarction (P for trend across quartiles, 0.005) and cardiovascular death (P for trend across quartiles, 0.001) (Table 3). Results were similar with or without adjustment for baseline differences between cases and controls including conventional vascular risk factors, co-interventions, and randomised treatment allocation.

To evaluate whether increased baseline urinary 11-dehydro thromboxane $B_2$ concentrations were associated with early rather than late cardiovascular events separate analyses were performed in patients who experienced an event within the first 12 months of study entry and those whose event occurred more than 12 months after study entry. The adjusted odds for the composite outcome of myocardial infarction, stroke, or cardiovascular death that was associated with the highest quartile of urinary 11-dehydro thromboxane $B_2$ as compared with the lowest quartile was 2.9 (95% Cl: 0.9-9.1) for events occurring with the first 12 months and 1.7 (95% Cl: 1.0-2.7) for events occurring after the first 12 months.

Using linear multivariable regression modeling, variables that were found to be independently associated with baseline urinary 11-dehydro thromboxane $B_2$ concentrations in the urine were: female gender (P=0.004); body mass index (P=0.001), history of peripheral vascular disease (P=0.01), current cigarette smoking (P=0.09), use of calcium channel blockers (P=0.08), and randomisation to vitamin E (P=0.04). However, these variables combined were able to predict less than 5% of the variation in urinary 11-dehydro thromboxane $B_2$ concentrations (R-square 0.045).

These results indicate that urinary thromboxane B2 levels can be used an indicator of aspirin resistance and that aspirin resistance is a valuable predictor of the occurrence of a cardiovascular event.

TABLE 1

Baseline characteristics of study participants.*

| Characteristic† | Cases (n = 488) | Controls (n = 488) | P-value |
|---|---|---|---|
| Age - yr | 67.3 ± 7.2 | 67.4 ± 7.2 | 0.78 |
| Female sex - no. (%) | 77 (15.8) | 77 (15.8) | — |
| Body mass index‡ | 27.8 ± 4.1 | 26.9 ± 3.7 | <0.001 |
| Heart rate - beats/min | 66.2 ± 10.3 | 65.6 ± 10.9 | 0.41 |
| SBP - mm Hg | 137.1 ± 20.6 | 133.5 ± 18.0 | 0.002 |
| DBP - mm Hg | 76.6 ± 9.8 | 75.6 ± 9.4 | 0.08 |
| History of coronary disease - no. (%) | | | |
| Any | 469 (96.1) | 464 (95.1) | 0.54 |
| MI | 364 (74.6) | 309 (63.4) | <0.001 |
| Stable angina | 355 (72.7) | 336 (68.9) | 0.19 |
| Unstable angina | 184 (37.7) | 176 (36.1) | 0.65 |
| CABG | 176 (36.1) | 154 (31.6) | 0.15 |
| PCI | 87 (17.8) | 104 (21.3) | 0.22 |
| Stroke or TIA - no. (%) | 59 (12.1) | 40 (8.2) | 0.06 |
| Peripheral vascular disease - no. (%) | 240 (49.2) | 173 (35.5) | <0.001 |
| Hypertension - no. (%) | 219 (44.9) | 154 (31.6) | <0.001 |
| Diabetes - no. (%) | 159 (32.6) | 105 (21.5) | <0.001 |
| Elevated total cholesterol - no. (%) | 279 (57.2) | 310 (63.5) | 0.38 |
| Current cigarette smoking - no. (%) | 81 (16.6) | 57 (11.7) | 0.03 |
| Medications - no. (%) | | | |
| Aspirin | 488 (100) | 488 (100) | — |
| β-blocker | 241 (49.4) | 235 (48.2) | 0.76 |
| Lipid-lowering agent | 121 (24.8) | 166 (34.0) | 0.002 |
| Diuretics | 73 (15.0) | 34 (7.0) | <0.001 |
| Calcium channel blockers | 289 (59.2) | 238 (48.8) | 0.002 |
| Ramipril | 227 (46.5) | 274 (56.1) | 0.003 |
| Vitamin E | 246 (50.4) | 252 (51.6) | 0.74 |

*Plus-minus values are mean ± SD.
†CABG denotes coronary artery bypass graft surgery, CV cardiovascular, DBF diastolic blood pressure, MI myocardial infarction, PCI percutaneous coronary intervention, SBP systolic blood pressure, TIA transient ischaemic attack.
‡The body-mass index is the weight in kilograms divided by the square of the height in meters.

TABLE 2

Baseline urinary concentrations of urinary 11-dehydro thromboxane $B_2$ in cases and contr ls.

| Outcome | 11-dehydro thromboxane $B_2$ concentration (ng/mmol creatinine) | | |
|---|---|---|---|
| | Cases | Controls | P-value |
| MI, Stroke or CV death (n = 488) | | | |
| Geometric mean | 24.5 | 21.5 | 0.01 |
| Median | 22.7 | 21.0 | 0.01 |
| MI (n = 378) | | | |
| Geometric mean | 24.5 | 20.9 | 0.003 |
| Median | 22.8 | 20.3 | 0.001 |
| Stroke (n = 80) | | | |
| Geometric mean | 25.0 | 27.4 | 0.47 |
| Median | 21.3 | 25.9 | 0.40 |
| CV death (n = 244) | | | |
| Geometric mean | 25.6 | 20.4 | <0.001 |
| Median | 24.0 | 19.9 | <0.001 |

MI denotes myocardial infarction, CV cardiovascular.

TABLE 3

Adjusted odds* of future cardiovascular death, myocardial infarction, and stroke according to baseline urinary concentrations of 11-dehydro thromboxane $B_2$.

| Outcome† | Quartiles of 11-dehydro thromboxane $B_2$ concentration (ng/mmol creatinine) | | | | P for trend |
|---|---|---|---|---|---|
| | <15.1 | 15.1-21.8 | 21.9-33.7 | >33.7 | |
| MI/Stroke/CV death (n = 488) | | | | | |
| Odds ratio (95 CI) | 1.0 | 1.3 (0.9-2.0) | 1.4 (0.9-2.2) | 1.8 (1.2-2.7) | 0.01 |
| P-value | — | 0.13 | 0.09 | 0.009 | |
| MI (n = 378) | | | | | |
| Odds ratio (95 CI) | 1.0 | 1.3 (0.8-2.1) | 1.5 (1.0-2.5) | 2.0 (1.2-3.4) | 0.005 |
| P-value | — | 0.26 | 0.07 | 0.006 | |
| Stroke (n = 80) | | | | | |
| Odds ratio (95 CI) | 1.0 | 2.5 (0.6-10.0) | 0.6 (0.2-2.2) | 0.6 (0.2-1.8) | 0.20 |
| P-value | — | 0.18 | 0.45 | 0.34 | |
| CV death (n = 244) | | | | | |
| Odds ratio (95 CI) | 1.0 | 2.0 (1.0-3.9) | 2.5 (1.3-4.9) | 3.5 (1.7-7.4) | 0.001 |
| P-value | — | 0.06 | 0.006 | <0.001 | |

*Adjusted for baseline differences between cases and controls.
†CI denotes confidence interval, MI myocardial infarction, CV cardiovascular.

REFERENCES

1. Eikelboom J. et al. Aspirin resistance and the risk of myocardial infarction, stroke, or cardiovascular death in patients at high risk for cardiovascular events. *Circulation* 2002; 105:1650.

We claim:

1. An immunoassay kit for detecting an analyte in a test sample, comprising:
   i. a first strip including a test patch that contains a predetermined amount of an antibody specifically binding to the analyte, wherein the antibody is linked to a reporter molecule capable of releasing a signal, and
   ii. a second strip made of an absorbent material for absorbing the test sample the second strip being configured to be separable from the first strip, wherein after contacting the first strip for a fixed time period with the second strip absorbed with the test sample and then separating them, the antibody bound to the analyte moves from the first strip to the second strip and the antibody not bound to the analyte remains on the first strip, the level of signal released from the reporter molecule linked to the antibody remaining on the first strip being inversely proportional to the amount of the analyte in the test sample.

2. The immunoassay kit of claim 1, wherein the first strip further includes four reference patches containing four predetermined amounts of the reporter molecule, the levels of signal released therefrom corresponding to four determined concentrations of the analyte.

3. The immunoassay kit of claim 1, wherein the reporter molecule is a dye.

4. The immunoassay kit of claim 1, wherein the reporter molecule is an enzyme.

5. The immunoassay device according to claim 1, wherein the antibody binds to thromboxane B2.

6. The immunoassay kit according to claim 5, wherein the first strip further includes four reference patches containing four predetermined amounts of the reporter molecule, the level of signal released therefrom corresponding to relative risks of a cardiovascular event.

7. The immunoassay kit according to claim 6, wherein the levels of signal released from the four predetermined amounts of the reporter molecule correspond to the following four amounts of urinary 11-dehydro thromboxane B2: (i) less than 15.1 ng/mmol creatinine, (ii) 15.1-21.8 ng/mmol creatinine, (iii) 21.9-33.8 ng/mmol creatinine, and (iv) higher than 33.8 ng/mmol creatinine.

8. The immunoassay kit according to claim 6, wherein the reporter molecule is a dye.

9. The immunoassay kit according to claim 6, wherein the reporter molecule is an enzyme.

* * * * *

UNITED STATES PATENT AND TRADEMARK OFFICE
CERTIFICATE OF CORRECTION

PATENT NO.       : 7,595,201 B2                             Page 1 of 1
APPLICATION NO.  : 10/670118
DATED            : September 29, 2009
INVENTOR(S)      : Yusuf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 763 days.

Signed and Sealed this

Fourteenth Day of December, 2010

David J. Kappos
*Director of the United States Patent and Trademark Office*